United States Patent [19]

Diamond et al.

[11] 4,353,921

[45] Oct. 12, 1982

[54] ANTIARRYTHMIC 1-ARYLCARBAMOYLALKYL-2-IMIDAZOLINE DERIVATIVES, COMPOSITION AND METHOD OF USE

[75] Inventors: Julius Diamond, Mountain Lakes; Thomas K. Morgan, Jr.; Ronald A. Wohl, both of Morris Plains, all of N.J.

[73] Assignee: Berlex Laboratories, Inc., Cedar Knolls, N.J.

[21] Appl. No.: 275,172

[22] Filed: Jun. 19, 1981

[51] Int. Cl.³ ............... A61K 31/415; C07D 233/81; C07D 233/06; C07D 233/20
[52] U.S. Cl. .................. 424/273 R; 548/341; 548/352
[58] Field of Search .................. 548/341, 352; 424/273 R

[56] References Cited

U.S. PATENT DOCUMENTS

| | | | |
|---|---|---|---|
| 4,073,923 | 2/1978 | Balasubzamanyan et al. | 424/273 R |
| 4,287,210 | 9/1981 | Eckhardt et al. | 548/341 |
| 4,292,429 | 9/1981 | Marxer | 548/352 |

FOREIGN PATENT DOCUMENTS 2847287  5/1980  Fed. Rep. of Germany .

OTHER PUBLICATIONS

Ikura et al., Chem. Abst. 1980, vol. 92, No. 58776y (+index pages).

*Primary Examiner*—Henry R. Jiles
*Assistant Examiner*—N. Harkaway
*Attorney, Agent, or Firm*—Elizabeth A. Bellamy; John L. White; I. William Millen

[57] ABSTRACT

Novel 1,2-disubstituted imidazol(in)es are described herein. The compounds are generally produced by reacting a haloacylanilide with an excess of 2-substituted-imidazol(in)e. The compounds are antiarrhythmic agents.

14 Claims, No Drawings

ANTIARRYTHMIC 1-ARYLCARBAMOYLALKYL-2-IMIDAZOLINE DERIVATIVES, COMPOSITION AND METHOD OF USE

FIELD OF THE INVENTION

This invention relates to novel compositions, to methods for their manufacture and methods for their use. Specifically, this invention relates to novel 1,2-disubstituted imidazol(in)es more especially to that 1,2-disubstitution which is accomplished by reacting a haloacylanilide with a 2-substituted-imidazole(in)e. The compounds thus produced, inclusive of their pharmaceutically acceptable acid addition salts, are useful as antiarrhythmic agents.

GENERAL DESCRIPTION OF THE INVENTION

COMPOSITION-OF-MATTER ASPECT

In its composition of matter aspect, this invention relates to novel 1,2-disubstituted imidazol(in)es. Particularly, this invention relates to the novel compounds defined by the following Formula I:

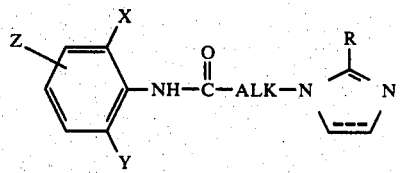

wherein
- R = $C_1$–$C_8$ alkyl, phenyl, benzyl, substituted phenyl, $C_3$–$C_7$ cycloalkyl, $C_4$–$C_8$ cycloalkylalkyl;
- X = $C_1$–$C_4$ alkyl, fluoro, chloro, bromo, trifluoromethyl;
- Y = hydrogen, $C_1$–$C_4$ alkyl, fluoro, chloro, bromo;
- Z = hydrogen, hydroxy, fluoro, chloro, bromo, methyl, $C_1$–$C_4$ alkoxy, $C_1$–$C_4$ acyloxy;
- ALK = straight or branched chain alkylene having up to 8 carbon atoms;
- --- = the dotted line represents the presence or absence of a double bond; and the pharmaceutically acceptable acid addition salts thereof.

The compounds of this invention wherein R is $C_1$–$C_8$ alkyl are defined as those wherein R is a straight or branched chain alkyl having up to 8 carbon atoms e.g. methyl, ethyl, propyl, isopropyl, butyl, tert-butyl and higher homologs such as pentyl, hexyl, heptyl, and octyl. Those compounds wherein R is substituted phenyl are defined as those wherein the phenyl group is monosubstituted by $C_1$–$C_4$ alkyl, cyano, bromo, chloro, fluoro, hydroxyl, $C_1$–$C_4$ alkoxy. In those instances wherein $C_1$–$C_4$ alkyl, alkoxy and acyloxy are referred to, $C_1$–$C_4$ is taken to mean straight or branched chain groups.

More preferred compounds of this invention are those defined by the following Formula II:

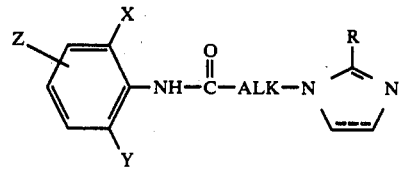

wherein R, X, Y, Z and ALK are as defined in Formula I. Some of the still more preferred compounds of this invention are those within Formula II wherein in each separate instance.

(a) Z is hydrogen;
(b) X and Y are $C_1$–$C_4$ alkyl;
(c) R is $C_1$–$C_8$ alkyl;

The most preferred compounds of this invention are those of Formula II wherein X, Y, & R are methyl.

The following are some of the compounds which exemplify various aspects of the invention described herein.

(1) 2-methyl-1-[(2,6-dimethylphenyl)carbamoylmethyl]imidazole
(2) 2-ethyl-1-[(2,6-dimethylphenyl)carbamoylmethyl]-2-imidazoline
(3) 1-[(2-ethyl-6-methylphenyl)carbamoylmethyl]-2-methyl-2-imidazoline
(4) 2-methyl-1-[(2,6-dimethylphenyl)carbamoylmethyl]-2-imidazoline
(5) 2-methyl-1-[1-[(2,6-dimethylphenyl)carbamoyl]ethyl]-2-imidazoline
(6) 2-methyl-1-[2-[(2,6-dimethylphenyl)carbamoyl]ethyl]-2-imidazoline
(7) 2-methyl-1-[1-methyl-2-[(2,6-dimethylphenyl)carbamoyl]ethyl]-2-imidazoline
(8) 2-methyl-1-[2-methyl-2-[(2,6-dimethylphenyl)carbamoyl]ethyl]-2-imidazoline Included also within the composition-of-matter aspect of the invention are the pharmaceutically acceptable acid addition salts of the 1,2-disubstituted imidazol(in)es. The pharmaceutically acceptable acid addition salts contemplated are prepared according to known procedures and are those derived from, for example, the following acids, hydrochloric, hydrobromic, sulphuric, phosphoric, acetic, propionic, benzoic, naphthoic, oxalic, succinic, maleic, malic, adipic, lactic, tartaric, citric, salicylic, methanesulphonic and p-toluenesulphonic.

PROCESS ASPECT

The compounds of the present invention can be prepared by a number of different methods. In the preferred method, a haloacylanilide of the following Formula III:

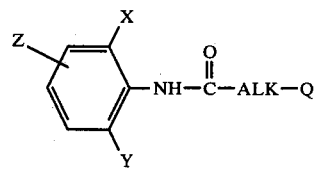

is reacted, in an aprotic solvent such as nitromethane at room temperature, with about a five fold excess of the 2-substituted-imidazole or 2-substituted-imidazoline of the Formula IV:

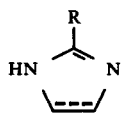

wherein X, Y, Z, R, ALK and -- are as defined herein and Q is halogen, preferably chlorine or bromine. When equivalent quantities of the above reactants are used considerable bis-alkylation of the imidazol(in)e takes place. In order to reduce the bis-alkylation, an excess, preferably about a five fold excess of the heterocycle, is used.

In an alternate process, for the preparation of certain β-imidazol(in)yl-anilides of Formula I, the imidazol-(in)e is reacted with an α, β-unsaturated acylanilide of the Formula V:

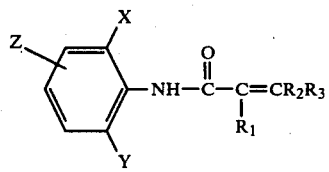

wherein X, Y, & Z are defined as above and $R_1$, $R_2$, $R_3$ are hydrogen or alkyl groups, with the proviso that $R_1$, $R_2$, $R_3$ cannot together be hydrogen. This process is carried out in a pressure apparatus at temperature from about 50° C. to about 200° C., in the presence or absence of solvents, preferably utilizing acid catalysis. Solvents suitable for the process are aqueous alcohol, abs. ethanol and higher alcohols, etc; suitable acid catalysts are sulphuric acid, methanesulphonic acid and p-toluenesulphonic acid.

In still another process, to prepare imidazolines of Formula II, a haloacylanilide of Formula III is reacted with ethylenediamine or a N-protected ethylenediamine of the Formula:

H₂NCH₂CH₂NR₄Prot.
Where R₄=H, Prot.
Prot.=benzyl etc,

wherein R is as defined in Formula I; with the proviso that when Prot. is

then R₄ must be hydrogen, to obtain a compound of the Formula VI:

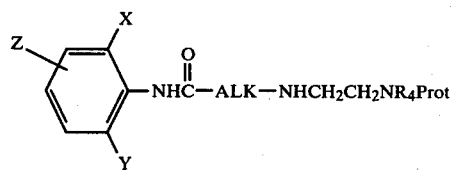

The resultant intermediate VI, when R₄ is H and Prot. is

can be cyclized directly to a product of the Formula II, e.g. by heat, Lewis acids and/or dehydrating agents. When R₄ and Prot. are either or both protecting groups other than

then these must be removed before cyclization to the 2-imidazoline can take place. The cyclization is accomplished by known reagents and conditions. R will determine which reagents such as carboxylic acids, carboxylic esters, imidate esters or orthoesters are to be used. Reaction conditions will utilize Lewis acids, heat and dehydrating agents where applicable.

METHOD-OF-USE AND PHARMACEUTICAL COMPOSITION ASPECT

The compounds of this invention and their pharmaceutically acceptable acid addition salts are useful as antiarrhythmic agents. Their antiarrhythmic activity was demonstrated by their effect against different types of cardiac arrhythmias in standard test procedures. Primarily, the antiarrhythmic activity was determined in mongrel dogs 24 and/or 48 hours past myocardial infarction via the well known method of A. S. Harris [Circulation 1, 1318 (1950)]. It has been determined that the compounds of Formula I, preferentially those of Formula II, best exemplified by 2-methyl-1-[(2,6-dimethylphenyl)carbamoylmethyl]imidazole and 2-methyl-1-[2-[(2,6-dimethylphenyl)carbamoyl]ethyl]-2-imidazoline were effective in suppressing ventricular arrhythmias in the dose range 0.5–20 mg/kg.

In general, the compounds of this invention may be administered orally or parenterally. The dosage administered will be dependent on the age and weight of the mammalian species being treated, the route of administration and the type and severity of the arrhythmia being prevented or reduced.

When administered orally, compounded in the form of tablets or capsules the dosage will usually be from about 4 to about 30 mg/kg of body weight per day divided into about 1 to 4 doses.

When administered parenterally, via intramuscular or intravenous injection the dosage will usually be from about 5 to about 30 mg/kg of body weight per day divided into about 2 to 4 doses.

The non-toxic pharmaceutical carriers useful in the preparation of all the foregoing formulations will include, for example, such substances as water, oils, fats, waxes, polyesters, alcohols, polyols and the like.

The invention described herein is illustrated below in the Examples, which is not to be construed as limiting the scope of this invention.

EXAMPLE I

A.

2-Methyl-1-[(2,6-dimethylphenyl)carbamoylmethyl]-2-imidazoline

To a solution of 10.0 gm. (0.05 M) of 2-chloro-2',6'-acetoxylidide in 100 ml. of nitromethane add 21.35 gm (0.254 M) of lysidine. Stir the solution at room temperature for about 17 hours. Follow the progress of the reaction by thin layer chromatography on silica gel (acetonitrile: ammonium hydroxide: methanol, 85:10:5). At the completion of the reaction, remove the solvent in vacuo, to the residue add 150 ml. of water, adjust the pH to about 7.0 with conc. hydrochloric acid. Extract the resultant solution with 3×100 ml. methylene chloride and discard. Adjust the pH of the water layer to about 11–11.5 with 50% sodium hydroxide. Extract with 4×200 ml. of methylene chloride. Take the combined latter extracts and wash 3×50 ml. of water. Dry the methylene chloride extracts over $Na_2SO_4$. Evaporate the solvents to provide the title compound.

NMR $(CDCl_3)$: $\delta = 1.88(s,3)$, 2.13(s,6), 3.10–3.75(m,4), 3.81(s,2), 7.04(s,3) and 9.04(bs,1)ppm.

B.

2-Methyl-1-[(2,6-dimethylphenyl)carbamoylmethyl]-2-imidazoline benzoic acid salt Dissolve the product of IA in 100 ml. of isopropanol, add 1.05 equivalents of benzoic acid, heat to reflux, add more isopropanol to obtain solution. Remove solution from reflux, let cool and add ether and chill. Filter product and wash with 1:1 isopropanol-ether, then ether. Dry solid in vacuo to obtain the title compound:

NMR $(DMSO-d_6)$: $\delta = 2.20(s,6)$, 2.25(s,3), 3.76(bs,4), 4.42(bs,2), 7.11(s,3), 7.37(m,3, benzoic acid), 7.95(m,2,benzoic acid), 9.79(bs,1), and 10.40(bs,1)ppm.

EXAMPLE II

A.

2-Methyl-1-[1-[(2,6-dimethylphenyl)carbamoyl]ethyl]-2-imidazoline

In a manner similar to Example IA react 15.88 gm. (0.075 M) of 2-chloro-N-(2,6-dimethylphenyl)propionamide with 31.55 gm. (0.375 M) of lysidine in 150 ml. of nitromethane to obtain the title compound.

B.

2-Methyl-1-[1-[(2,6-dimethylphenyl)carbamoyl]ethyl]-2-imidazoline phosphoric acid salt hemimethanolate Dissolve 11.31 gm. of Ex. IIA in 50 ml. of ethanol and add with stirring 45 ml. of 1 N phosphoric acid in ethanol. Chill the resultant mixture overnight. Filter the precipitate, wash with ethanol and air dry. Triturate the solid in about 100 ml. of ethanol at reflux for about 15 minutes, cool, filter, wash the solid with ethanol and air dry:

NMR $(D_2O, TMS$ ext.): $\delta = 2.16(d,3)$, 2.66(s,6), 2.76(s,3), 4.23(m,4), 5.34(q,1) and 7.67(s,3) ppm.

EXAMPLE III

A.

2-Methyl-1-[2-[(2,6-dimethylphenyl)carbamoyl]ethyl]-2-imidazoline

In a manner similar to Ex. IA react 5.29 gm. (0.025 M) of 3-chloro-2',6'-propionoxylidide with 10.53 gm. (0.125 M) of lysidine in 200 ml. of anhydrous ethanol to obtain the title compound.

B.

2-Methyl-1-[2-[(2,6-dimethylphenyl)carbamoyl]ethyl]-2-imidazoline benzoic acid salt Dissolve 6.6 gm. of Ex. IIIA in 20 ml. of methylene chloride and to it add a solution of 3.0 gm. of benzoic acid in 20 ml. of ether. Filter the solid and recrystallize from isopropanol and ether, dry in vacuo:

NMR $(DMSO-d_6)$: $\delta = 2.17(s,6,2CH_3),2.24(s,3,N—C(CH_3)=N)$, 2.5-2.9(m,2), 3.5–3.9(m,6), 4.2(s,$H_2O$), 7.08(s,3), 7.2–7.5(m,3), 7.7–8.0(m,2) ppm.

EXAMPLE IV

A.

1-[(2-Ethyl-6-methylphenyl)carbamoylmethyl]-2-methyl-2-imidazoline.

In a manner similar to Ex. IA react 21.17 gm. (0.1 M) of 2-chloro-2'-ethyl-6'-methylacetanilide and 42.1 gm. (0.5 M) of lysidine in 250 ml. of nitromethane, to obtain the title compound:

NMR $(CDCl_3)$: $\delta = 1.16(t,3)$, 1.97(s,3), 2.18(s,3), 2.54(q,2), 3.10–3.70(m,4), 3.87(s,2), 7.15 (s,3) and 8.78(bs,1)ppm.

EXAMPLE V

A.

2-Ethyl-1-[(2,6-dimethylphenyl)carbamoylmethyl]-2-imidazoline

In a manner similar to Ex. IA react 47.7 gm. (0.486 M) of 2-ethyl-2-imidazoline and 19.21 gm. (0.097 M) of 2-chloro-2',6'-acetoxylidide in 200 ml. of nitromethane, to obtain the title compound.

B.

2-Ethyl-1-[(2,6-dimethylphenyl)carbamoylmethyl]-2-imidazoline benzoic acid salt

Dissolve 15 gm. of Ex. VA and 7.55 gm. of benzoic acid in 120 ml. of ethanol with heating. Reduce in vacuo most of the solvent. To the residue add 50 ml. of isopropanol and heat to reflux, then add about 10 ml. of ether and chill. Filter the product and wash with water, 1:1 isopropanol and ether, air dry to obtain the title compound:

NMR $(DMSO-d_6)$: $\delta = 1.17(t,3)$, 2.20(s,6), 2.56(q,2), 3.76(bs,4), 4.42(bs,2), 7.12(s,3), 7.40(m,3,benzoic acid), 7.96(m,2,benzoic acid), 8.81(bs,1), and 10.37(bs,1)ppm.

EXAMPLE VI

A.

2-Methyl-1-[(2,6-dimethylphenyl)carbamoylmethyl]imidazole

Combine 19.78 gm. (0.1 M) of 2-chloro-2'-6'-acetoxylidide and 41.05 gm. (0.5 M) of 2-methylimidazole and stir at about 140°–160° C. under nitrogen for about 2.5 hours. Quench reaction mixture with about 500 ml. of water, then chill with stirring in a ice/water bath. Filter the precipitate and recrystallize from an ethanol/water mixture. Air dry to obtain the title compound.

B.

2-Methyl-1-[(2,6-dimethylphenyl)carbamoylmethyl]imidazole Hydrochloride

Dissolve 3.7 gm. (15.2 mM) of Ex. VIA in about 40 ml. of warm ethanol. To this solution add 2.1 ml. (about 25 mM) conc. hydrochloric acid. Remove the solvent in vacuo, crystallize the residue from acetonitrile, filter, dry in vacuo.

NMR $(D_2O, TMS$ Ext.): $\delta = 2.64(s,6)$, 3.06(s,3), 5.69(s,2), 7.60(s,3), 7.78(d,1), and 7.84 (d,1)ppm.

EXAMPLE VII

A.
2-Methyl-1-[1-methyl-2-[(2,6-dimethylphenyl)carbamoyl]ethyl]-2-imidazoline Combine 1.89 gm. (0.01 M) N-(2,6-dimethylphenyl)-crotonamide, 0.90 gm. (0.0107 M) lysidine, 0.01 gm. (~0.001 M) methanesulphonic acid and about 40 ml. of ethanol in a pressure bottle and heat (bath temp. 100°–110° C.) for about 100 hours. Remove the solvent in vacuo, add about 50 ml. of water. Adjust the pH to 8.0 with concentrated HCl, and extract the aqueous phase with 2×25 ml. methylene chloride. Then adjust the aqueous phase to pH 13 with 50% sodium hydroxide and extract with 3×30 ml. of methylene chloride. Wash the combined methylene chloride extracts with 2×5 ml. of water. Dry the methylene chloride extracts over sodium sulfate. Evaporate off the solvents to obtain the title compound.

NMR (CDCl$_3$): δ=1.05(d,3), 1.74(s,3), 2.06(s,6), 2.20–2.60(m,2), 2.85–3.80(m,4), 4.05(m,1), 7.00(s,3), and 9.77(bs,1)ppm.

EXAMPLE VIII

A.
2-Methyl-1-[2-methyl-2-[(2,6-dimethylphenyl)carbamoyl]ethyl]-2-imidazoline Combine 30.0 gm. (0.16 M) N-(2,6-dimethylphenyl)-2-methylpropenamide [methacroyl-2',6'-xylidide], 13.3 gm. (0.16 M) lysidine, 3 gm. (0.03 M) methanesulphonic acid and 150 ml. of ethanol in a pressure bottle and heat at about 150° C. for about 48 hours. Remove the solvent in vacuo, add 200 ml. of water and adjust the pH to 7.8 with conc. HCl. Extract the aqueous phase with 4×100 ml. of methylene chloride and set these aside. Treat the aqueous phase with 20% NaOH to obtain a pH of about 13. Extract the aqueous phase with 4×100 ml. of methylene chloride. Wash the combined methylene chloride extracts with 3×10 ml. water and dry organic layer over sodium sulfate. Evaporate off the solvents to obtain the title compound.

B.
2-Methyl-1-[2-methyl-2-[(2,6-dimethylphenyl)carbamoyl]ethyl]-2-imidazoline (1:1) oxalic acid salt hydrate Dissolve 5.3 gm. (0.019 M) of Example VIII and 2.4 gm. (0.021 M) of oxalic acid in 20 ml. of ethanol. Remove the solvent in vacuo, triturate with acetonitrile and refrigerate. Decant solvent, triturate twice with ether, filter and dry in vacuo.

NMR (DMSO-d$_6$): δ=1.15(d,3,CH$_3$); 2.1(s,6,Ar-CH$_3$); 2.2

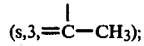
(s,3,=C—CH$_3$);

2.8–3.8(m,8,CH+CH$_2$+OH); 7.1(s,3,Ar-H); 9.0–10.1(m,4)ppm.

EXAMPLE IX

OTHER SUBSTITUTED IMIDAZOL(IN)ES

A. haloanilide—imidazol(in)e—subst. imidazol(in)e
1. 2-chloro-2',6'-acetoxylidide+2-phenyl-2-imidazoline=1-[(2,6-dimethylphenyl)carbamoylmethyl]-2-phenyl-2-imidazoline.
2. 3-chloro-2'-chloro-6'-methylpropionanilide+lysidine=1-[(2-chloro-6-methylphenyl)carbamoylmethyl]-2-methyl-2-imidazoline.
3. 2-chloro-2',6'-acetoxylidide+2-(2-hydroxyphenyl)-2-imidazoline=2-(2-hydroxyphenyl)-1-[(2,6-dimethylphenyl) carbamoylmethyl]-2-imidazoline.
4. 2-chloro-2',6'-acetoxylidide+2-(p-cyanophenyl)-2-imidazoline=2-(p-cyanophenyl)-1-[(2,6-dimethylphenyl)-carbamoylmethyl]-2-imidazoline.
5. 3-chloro-2',6'-propionoxylidide+2-methylimidazole=2-methyl-1-[2-[(2,6-dimethylphenyl)carbamoyl]ethyl]imidazole.
6. 2-chloro-2',6'-acetoxylidide+2-ethylimidazole=2-ethyl-1-[(2,6-dimethylphenyl)carbamoylmethyl]imidazole.
7. 2-chloro-2',6'-propionoxylidide+2-methylimidazole=2-methyl-1-[1-[(2,6-dimethylphenyl)carbamoyl]ethyl]imidazole.
8. 3-chloro-2',6'-propionoxylidide+2-n-heptyl-2-imidazoline=2-n-heptyl-1-[2-[(2,6-dimethylphenyl)carbamoyl]ethyl]-2-imidazoline.
9. 3-chloro-N-(2,4,6-trimethylphenyl)propionamide+2-cyclopentyl-2-imidazoline=2-cyclopentyl-1-[2-[(2,6-dimethylphenyl)carbamoyl]ethyl]-2-imidazoline.

We claim:
1. A compound having the formula:

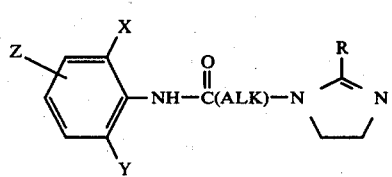

wherein
R=C$_1$–C$_8$ alkyl, phenyl, benzyl, substituted phenyl, C$_3$–C$_7$ cycloalkyl, C$_4$–C$_8$ cycloalkylalkyl
X=C$_1$–C$_4$ alkyl, fluoro, chloro, bromo, trifluoromethyl;
Y=hydrogen, C$_1$–C$_4$ alkyl, fluoro, chloro, bromo;
Z=hydrogen, hydroxy, fluoro, chloro, bromo, methyl, C$_1$–C$_4$ alkoxy, C$_1$–C$_4$ acyloxy;
ALK=straight or branched chain alkylene having up to 8 carbon atoms; and the pharmaceutically acceptable acid addition salts thereof.
2. A compound according to claim 1 wherein Z is hydrogen.
3. A compound according to claim 1 wherein X and Y are C$_1$–C$_4$ alkyl.
4. A compound according to claim 1 wherein R is C$_1$–C$_8$ alkyl.
5. A compound according to claim 1 wherein X, Y, and R are methyl.
6. A compound of claim 1 which is 2-ethyl-1-[(2,6-dimethyl-phenyl)carbamoylmethyl]-2-imidazoline.
7. A compound of claim 1 which is 1-[(2-ethyl-6-methylphenyl) carbamoylmethyl]-2-methyl-2-imidazoline.
8. A compound of claim 5 which is 2-methyl-1-[(2,6-dimethylphenyl)carbamoylmethyl]-2-imidazoline.
9. A compound of claim 5 which is 2-methyl-1-[1-[(2,6-dimethylphenyl)carbamoyl]ethyl]-2-imidazoline.
10. A compound of claim 5 which is 2-methyl-1-[2-[(2,6-dimethylphenyl)carbamoyl]ethyl]-2-imidazoline.

11. A compound of claim 5 which is 2-methyl-1-[1-methyl-2-[(2,6-dimethylphenyl)carbamoyl]ethyl]-2-imidazoline.

12. A compound of claim 5 which is 2-methyl-1-[2-methyl-2-[(2,6-dimethylphenyl) carbamoyl]ethyl]-2-imidazoline.

13. The method for the suppression of cardiac arrythmia in an animal which comprises administering to said animal an amount effective for the suppression of said arrythmia of a compound according to claim 1.

14. A pharmaceutical composition for the suppression of cardiac arrythmia comprising an anti-arrythmic effective amount of a compound of claim 1, together, with a non-toxic pharmaceutically acceptable carrier.

* * * * *

UNITED STATES PATENT AND TRADEMARK OFFICE
CERTIFICATE OF CORRECTION

PATENT NO. : 4,353,921

DATED : October 12, 1982

INVENTOR(S) : Julius Diamond, Thomas K. Morgan, Jr., Ronald Wohl

It is certified that error appears in the above-identified patent and that said Letters Patent is hereby corrected as shown below:

Column 2, line 7 " 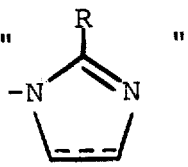 " should read -- 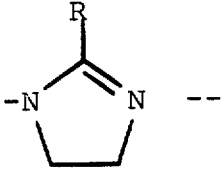 --

Column 3, line 31 "temperature" should read --temperatures--.
Column 7, line 49 "ethanol" should read --methanol--.

Signed and Sealed this

Sixth Day of March 1984

[SEAL]

Attest:

GERALD J. MOSSINGHOFF

Attesting Officer

Commissioner of Patents and Trademarks